United States Patent [19]
Kuramarohit

[11] Patent Number: 5,263,336
[45] Date of Patent: Nov. 23, 1993

[54] COOLING GARMENT

[76] Inventor: Kullapat Kuramarohit, P.O. Box 23 Maggasan P.O., Bangkok 10402, Thailand

[21] Appl. No.: 590,793

[22] Filed: Oct. 1, 1990

[30] Foreign Application Priority Data

Sep. 29, 1989 [AUST] Australia ............................ JP6678

[51] Int. Cl.⁵ .............................................. A61F 7/00
[52] U.S. Cl. ...................................... 62/259.3; 62/315; 62/316; 62/259.4; 62/310; 165/46; 607/104
[58] Field of Search ...................... 62/259.3, 315, 316, 62/310, 259.4; 165/46; 128/400

[56] References Cited
U.S. PATENT DOCUMENTS

| | | | |
|---|---|---|---|
| 594,209 | 11/1897 | Mears | 62/316 |
| 1,803,393 | 5/1931 | Jones | 62/316 |
| 3,017,888 | 1/1962 | Weiner | 62/259.3 |
| 3,029,438 | 4/1962 | Henschel | 62/259.3 |
| 3,079,765 | 3/1963 | Le Vantine | 62/259.3 |
| 3,212,286 | 10/1965 | Curtis | 62/259.3 |
| 3,429,138 | 2/1969 | Goldmerstein | 62/259.3 |
| 3,610,323 | 10/1971 | Troyer | 62/259.3 |
| 4,718,429 | 1/1988 | Smidt | 128/400 |

Primary Examiner—Albert W. Davis, Jr.
Attorney, Agent, or Firm—Wigman, Cohen, Leitner & Myers

[57] ABSTRACT

A portable personal cooling apparatus comprising: an exterior surface of fibrous material having a fluid holding capacity sufficient to allow continuous evaporation of a fluid; an interior surface of waterproof material adapted to avoid wetting of the object to be cooled from the fluid on the exterior surface; a fluid container on one of said surfaces for distributing the fluid to the fibrous material; a fluid collector on one of said surfaces for collecting the accumulated unevaporated fluid; at least one fluid return line for moving fluid in the fluid collector to the fluid container; and at least one of said return lines further including means for preventing fluid from flowing back from the fluid container to the fluid collector.

19 Claims, 3 Drawing Sheets 5,263,336

COOLING GARMENT

FIELD OF THE INVENTION

This invention relates to providing around the human body a contacting heat sink to absorb heat created by that body and thus cool the body down. In particular it relates to a special garment which is capable of being worn by a living body, and by evaporation of the fluid on its outer surface, it extracts body heat through a thin waterproof lining material present between the body and an outer-exposed to the air-liquid holding material, which is kept wet. For the sake of simplicity, the invention will be referred to as cooling garment.

BACKGROUND

Due to the inclination of 23.5 degrees of the Earth's rotational axis, the temperature of the air around us is varied from season to season through out the year, while the body temperature is at almost a constant one of about 37 degrees Celcius. When the air temperature increases to 28 degrees Celcius, we feel uncomfortably warm and start sweating. So the body needs the temperature of the medium next to its skin to be at least 9 degrees Celcius lower, to allow heat created by combustion inside the lungs to be transferred out of the body, or the process known to us as cooling down of ourselves. When the temperature of the air rises above 28 degrees Celcius the body excretes sweat through the surface of the skin to allow evaporation of the sweat. The latent heat of evaporation obtained from the body is used in changing the sweat from a liquid state to a vapour state thus allowing a second method of extracting heat from the body. When the air temperature increases further and even over the body temperature of 37 degrees celcius, e.g. 40 degrees, the first method of heat transfer ceases to exist and the heat, from the air, enters the body instead of exits from the body to the air. The body temperature thus increases to more than 37 degrees Celcius and automatically we fan ourselves. This is a third method of cooling out bodies down—increasing the air velocity passing over the wet skin to speed up the evaporation so that evaporation will release more heat from our bodies. This invention provides the means to do the sweating for our body and considerably cools the body. When other inventions, i.e. "room air control apparatus" and/or "localized air conditioning", are/is used in association with this cooling garment, the cooling increases many times and is ideal to cool the body during the hot seasons. The energy saving when compared with conventional refrigerating air conditioning is very great e.g. more than 2,000% in some cases. This also results in better health for the user of this or these invention/s, because there is a possibility to introduce 100% fresh air to the body all the time compared to the conventional system where stale air is recirculated with some small percentage of fresh air injected into the room being air conditioned.

OBJECTS OF THE INVENTION

The objects of this invention are to provide a cooling garment that has a liquid holding material on its outside for the purpose of achieving the evaporation of the liquid on its surface thereby reducing its temperature. Waterproof material on the inside prevents the body from being wet, but maintains close contact with the body or clothing worn over the body to extract heat from the body and to use such heat in its latent form to evaporate the liquid on the outside of the cooling garment. The invention also allows the wearer to replenish the liquid on the wet side of the cooling garment before the wet side dries up, as well as to maintain an even distibution of liquid over the wet surface. Also it aims to have a suitable liquid container of maximum size possible to reduce the frequency of refilling as well as to have a suitable liquid collector to collect the liquid at the bottom of the cooling garment. The collected liquid can then be pumped either manually or automatically back to the liquid container. Alternatively check valve/s can be used in place of the pump by reversing the positions of the container and collector to allow the liquid to reverse its flow under gravity back to the container from the collector. Also it aims to have the flexibility of attaching or detaching other cooling garment or portion/s of the cooling garment to the main cooling garment or to other part of the body such as leg/s, arm/s, foot/feet, hand/s or head etc.

SUMMARY OF THE INVENTION

Briefly described, the aforementioned objects are accomplished according to the present invention by providing a portable personal cooling apparatus comprising: an exterior surface of fibrous material having a fluid holding capacity sufficient to allow continuous evaporation of a fluid; an interior surface of waterproof material adapted to avoid wetting of the object to be cooled from fluid on the exterior surface; a fluid container means on one of said surfaces for distributing the fluid to the fibrous material; a fluid collector means on one of said surfaces for collecting accumulated unevaporated fluid; at least one fluid return line means for moving fluid in the fluid collector to the fluid container, at least one of said fluid return lines further including means for preventing fluid from flowing back from the fluid containers to the fluid collectors.

With the foregoing and other objects, advantages, and features of the invention which will become hereinafter apparent, the nature of the invention may be more clearly understood by reference to the following detailed description of the invention, the appended claims, and to the several views illustrated in the attached drawings.

BRIEF DESCRIPTION OF THE DRAWING FIGURES

The invention will now be described with reference to preferred embodiments as shown in the accompanying drawings in which.

PREFERRED EMBODIMENTS

Figure 1:
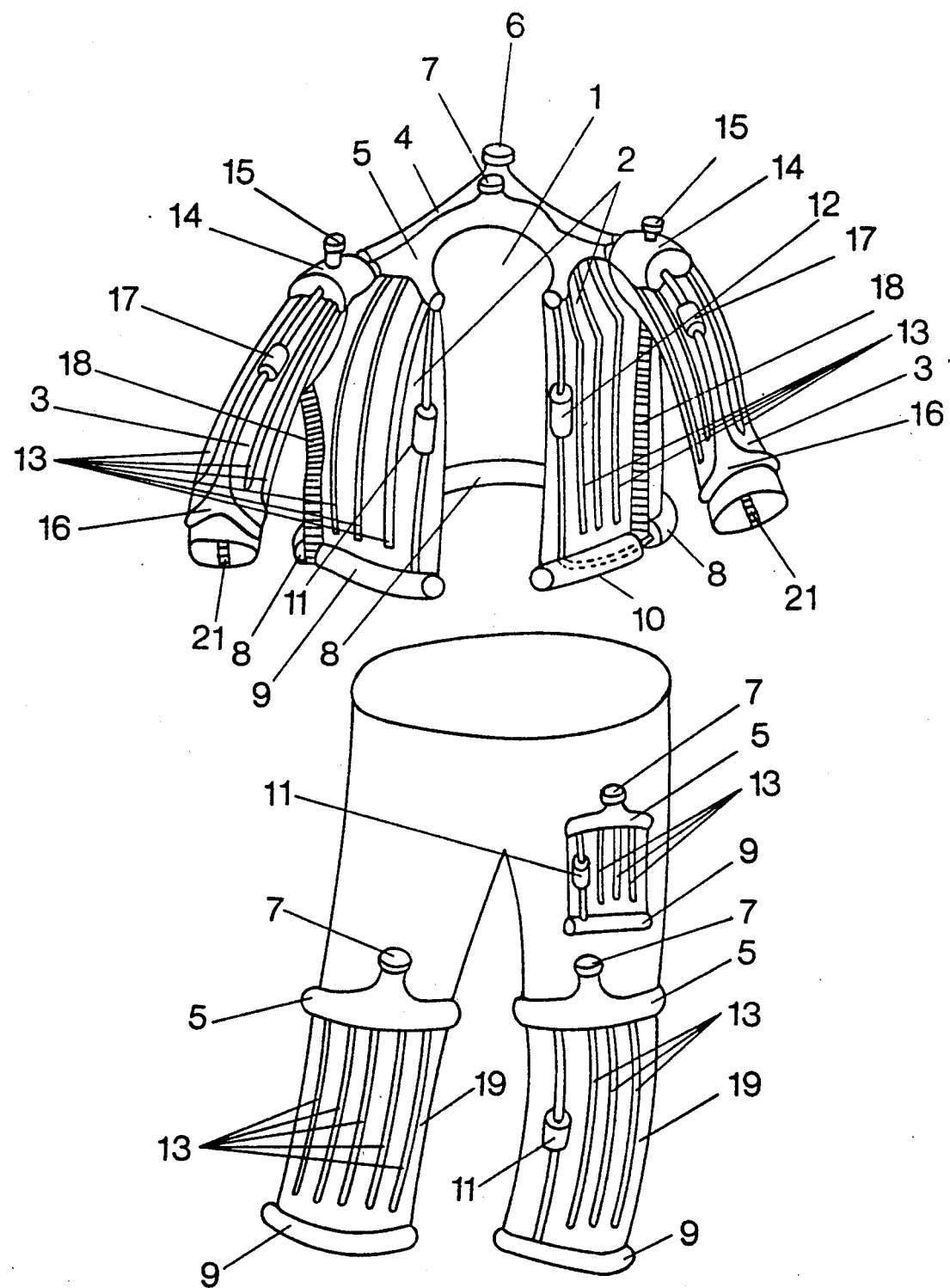
FIG. 1 is a schematic drawing of a coooling garment in accordance with the invention.

In FIG. 1, the jacket back portion 1, jacket front portions 2, attachable/detachable sleeves 3, leg garments 19 and small multilocation garment 20 are shown.

Figure 2:
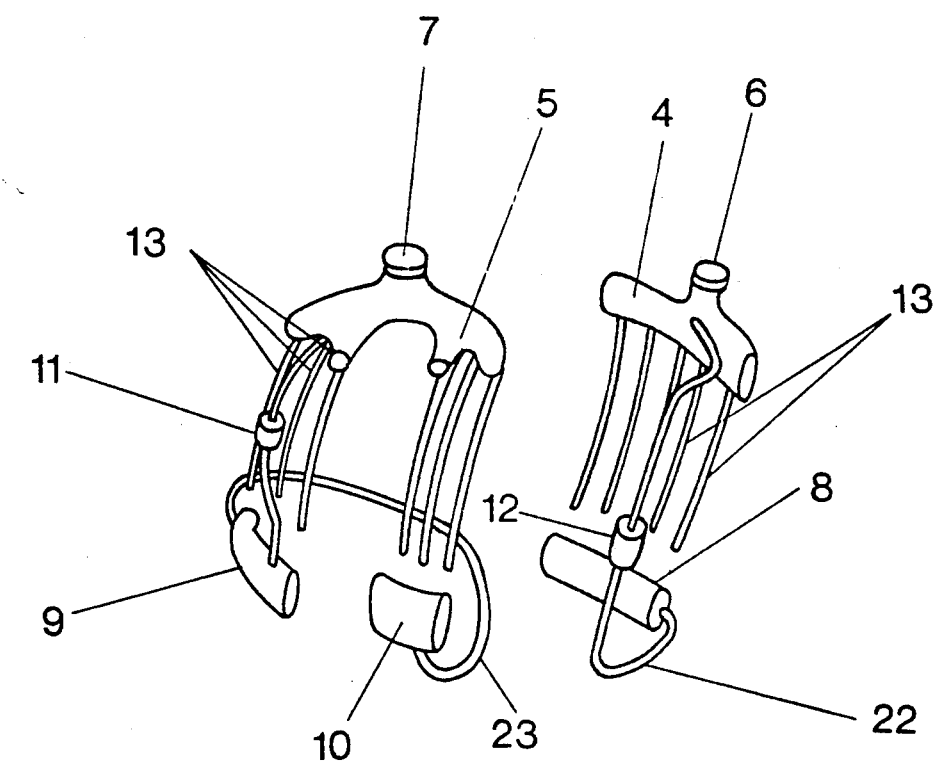
FIG. 2 is a schematic drawing of the liquid systems of the front portions of the jacket and the back portion of the jacket.

For jacket back portion 1, the components consist of: the outside surface made of fabric or felt materials (not shown in FIG. 1 but shown as 31 in FIG. 3), inside surface made of waterproof materials (not shown in FIG. 1 but shown in FIG. 3 as 32), the liquid container 4 having refilling neck with liquid tight cap 6, liquid collector 8 having the suction line 22 of pump 12 (or check valve) connected to it (shown passing inside liquid collector 10 of the jacket front portion 2 without communicating with the liquid in liquid collector 10 see also FIG. 2), pump 12 (or if a checkvalve is used to return the liquid in the liquid collector to the liquid container, the jacket must be turned upside down) having a discharge line connected to the liquid container 4 with check valve/s to prevent the liquid in the liquid container from flowing back to the collector, the distribution lines 13 (not shown in FIG. 1 but shown in FIG. 2), the body side waterproof material 18 (visible at the side seams where the felt or fabric materials of the front are separated from the back to prevent the liquid on both sides from seeping across to each other if it is desired to have the front side wet while keeping the back side dry or vice versa) and the outside felt or fabric material 31 (shown in FIG. 3) which protrudes inside the liquid container, liquid collector and distribution lines so that the liquid from the liquid collector 4 and liquid distribution lines 13 (shown in FIG. 2) can seep through to the fabric or felt, and from where such liquid seeps through the fabric or felt to the liquid collector.

For front jacket portions 2, the components are the same as the back jacket portion. The liquid container 5, liquid collectors 9 and 10 are separated from liquid container 4 and liquid collector 8 of the back jacket portion. The liquid collectors 9 and 10 are joined together by a line 23 between them (shown in FIG. 2) so that the liquid can be transported to liquid container 5 through the pump 11 (or check valve) drawing the liquid from both liquid collectors 9 and 10. Other components are the refilling neck and liquid tight cap 7 and liquid distribution lines 13.

For sleeves 3, the components are the same as those of the back portion of the jacket 1 and front portions of the jacket 2 except that pumps are replaced by check valves 17 and liquid can be transported from the liquid collectors 16 to the liquid containers 14 through the check valves 17 by the wearer raising his arms above shoulder height and letting gravity do its duty. The sleeves 3 are attachable/detachable to/from the jacket by any type of fastening mechanism preferred such as buttons and holes, zippers, tiny hooks and eyes of wool like materials etc. The other components are refilling neck and liquid tight cap 15 and distribution lines 13. The sleeves 3 can be transformed from cylindrical form to flat pieces of cooling garments by means of zippers 21 and can be used at other parts of the body such as legs etc. The underneath portions of the sleeves between the hands and elbows can be made without the felt or fabric so they will not be wet and wearer's forearms can come into contact with items such as table or paper on the table without wetting such items.

For leg garments 19 and flat cooling garment 20, the components are the same as the components of the front and back portions of the jacket. Thus they consist of the outside surface made of fabric or felt materials (not shown in FIG. 1 but shown in FIG. 3 as 31), the inside surface made of waterproof materials (not shown in FIG. 1 but shown in FIG. 3 as 32), the liquid containers 5 with refilling necks and the liquid tight caps 7, the liquid collectors 9, the pumps or check valves 11 (1 not shown incase of left leg garment) and the liquid distributor lines 13.

For all variations of the cooling garment, the working principle is the same. First the liquid container is filled with liquid and the cap secured. Then the liquid flows and disperses itself through the fabric or felt materials adjacent to the container and liquid distribution lines. The excess liquid which does not evaporate would gather at the bottom portion of the garment and drip away, wetting the clothing of the wearer if there were not liquid collector at the bottom. When the liquid is collected in sufficient quantity in the liquid collector, it is pumped back to the liquid container by squeezing the pump by hand or it is pumped automatically by a battery operated pump.

The evaporation of the liquid on the felt or fabric material will extract heat from the body of the wearer, thereby cooling him/her. When the wearer sits or stands in a place where there is wind blowing e.g. under a ceiling fan or near a standing fan, the rate of evaporation increases many times and the cooling process is maximised. To regulate the coolness, a higher wind velocity increases coolness, or alternatively the number of operating portion/s of the cooling garment can be increased or decreased or alternatively the liquid container on some piece/s of the garment can be left dry for warmer.

Figure 3:
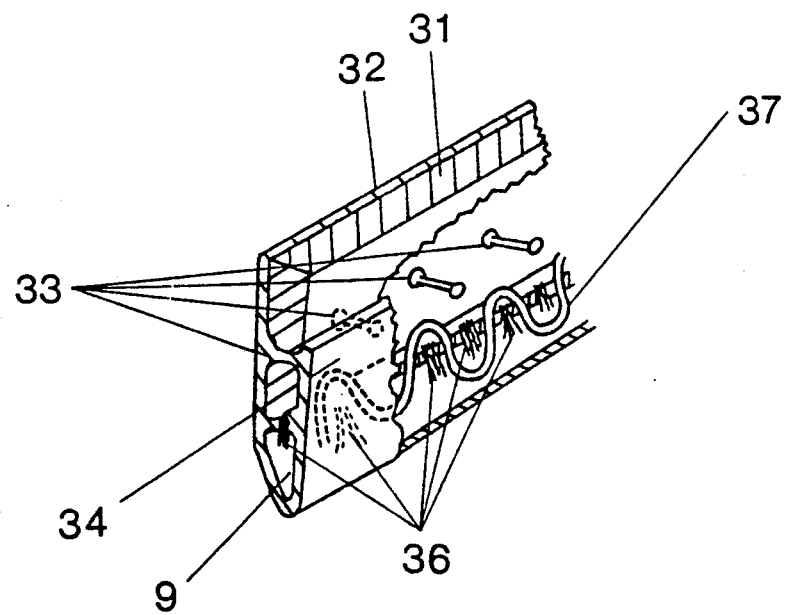
FIG. 3 is a detailed drawing showing how the liquid is collected at the liquid collector.

In FIG. 3, a detailed drawing of the liquid collector 9 is shown, with the outside wall 34 being higher up from the liquid collector body 9 to prevent over flowing of the liquid at the bottom of the fabric or felt materials where the concentration of the liquid will be highest and may exceed the holding ability of the fabric or felt materials so that dripping would occur if there were no outside wall. A row of stays 33 hold outside wall 34 to the inside waterproof lining materials 32 with the fabric or felt materials 31 in between. The liquid will drip through the felt or fabric materials 36 protruding inside the liquid collector 9. Seeping materials 37 may be employed to promote the liquid transfer from the felt or fabric materials to the liquid collector or vice versa in the case of the transfer from the liquid container to the felt or fabric materials.

Figure 4:
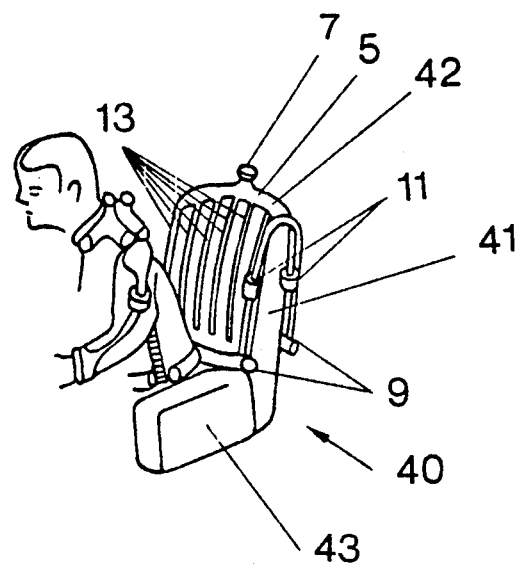
FIG. 4 is a perspective view of the application of the cooling garment or cooling patch to the back of the chair to creat another source of heat sink as well as protect the back of the chair from being wet.

In FIG. 4, a chair 40 having a backrest 41 covered by a cooling garment 42 where the evaporative surfaces are on both sides of the back rest as shown. The back rest 41 (including the seat) may be filled with liquid to have a greater heat sink capacity that the cooling garment continuously produces and intermittently used when the user leans against the backrest 41. The heat trapped at the seat can be carried away to the cooling garment and exchanged there. The cooling garment can be built in the chair and form the permanent chair cover not necessary at the back rest but can be at the arm rest 43 as well.

Figure 5:
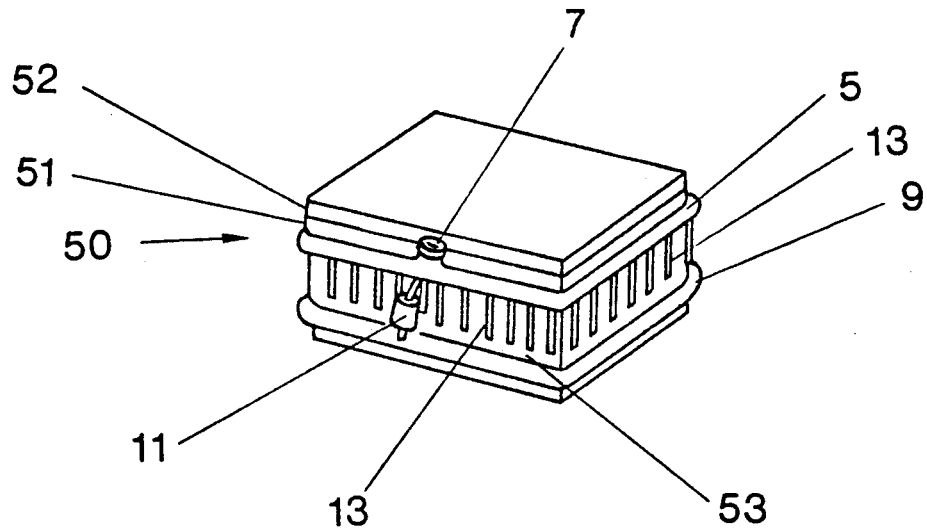
FIG. 5 is a perspective view of the application of the cooling garment to cool the ice box.

In FIG. 5, an ice box or animal cage 50, having the containing body 51 and lid 52, as shown. The cooling garment 53 is wrapped around the container 50 to provide the cooling effect to the thing inside or to reduce the coolness loss to the higher temperature ambient outside.

Although certain presently preferred embodiments of the invention have been described herein, it will be apparent to those skilled in the art to which the invention pertains that variations and modifications of the described embodiments may be made without departing from the spirit and scope of the invention. Accordingly, it is intended that the invention be limited only to the extent required by the appended claims and the applicable rules of law.

I claim:

1. Personal cooling apparatus comprising:
   an exterior surface of fibrous material having a length dimension and a fluid holding capacity sufficient to allow continuous evaporation of the fluid;
   an interior surface of waterproof material, having a continuous length the same as the exterior surface, adapted to prevent the object to be cooled from being wetted by fluid on the exterior surface;
   at least one elongated tubular fluid container positioned at an edge of said fibrous material, comprising means for distributing fluid to the fibrous material via an edge thereof, said fibrous material extending into the fluid container;
   at least one fluid collector means associated with one of said surfaces, for collecting accumulated unevaporated fluid;
   at least one return line means for moving the fluid in the fluid collector to the fluid container by gravitational force.

2. Apparatus as in claim 1, wherein said exterior surface has a length dimension, said interior surface has a continuous length dimension substantially the same as the exterior surface length dimension and further including at least one distribution line extending across the exterior surface from the fluid container.

3. Personal cooling apparatus as in claim 1, said exterior surface and said interior surface further including bodice and sleeve portions forming a jacket.

4. Personal cooling apparatus as in claim 3, further including at least one zip fastener running the length of each sleeve portion, wherein said sleeve portions are capable of being spread flat.

5. Personal cooling apparatus as in claim 3, wherein the sleeve portions are detachable from said bodice.

6. Personal cooling apparatus as in claim 3, wherein said jacket includes at least one front portion with at least one additional fluid container.

7. Personal cooling apparatus as in claim 1, further including a waterproof band extending around a base of the personal cooling apparatus, said band being adapted to prevent excess fluid from dripping from said personal cooling apparatus.

8. Personal cooling apparatus as in claim 7, including a plurality of fluid collectors joined together by tubes to enhance the draining of fluid at said base into the fluid collectors.

9. Personal cooling apparatus as in claim 1, further including means for affixing said personal cooling apparatus to a back rest of a chair.

10. Personal cooling apparatus comprising:
    an exterior surface of fibrous material having a length dimension and a fluid holding capacity sufficient to allow continuous evaporation of the fluid;
    at least one elongated tubular fluid container positioned at an edge of said fibrous material, comprising means for distributing fluid to the fibrous material via an edge thereof, said fibrous material extending into the fluid container;
    at least one fluid collector means associated with one of said surfaces, for collecting accumulated unevaporated fluid;
    at least one return line means for moving the fluid in the fluid collector to the fluid container by gravitational force; and
    at least one distribution line extending across the exterior surface from the fluid container.

11. Personal cooling apparatus as in claim 10, said exterior surface and said interior surface further including bodice and sleeve portions forming a jacket.

12. Personal cooling apparatus as in claim 11, further including at least one zip fastener running the length of each sleeve portion, wherein said sleeve portions are capable of being spread flat.

13. Personal cooling apparatus as in claim 11, wherein the sleeve portions are detachable from said bodice.

14. Personal cooling apparatus as in claim 11, wherein said jacket includes at least one front portion with at least one additional fluid container.

15. Personal cooling apparatus as in claim 10, further including a waterproof band extending around a base of the personal cooling apparatus and being adapted to prevent excess fluid from dripping from said personal cooling apparatus.

16. Personal cooling apparatus as in claim 15, including a plurality of fluid collectors joined together by tubes to enhance the draining of fluid at said base fluid collectors.

17. Personal cooling apparatus as in claim 10, further including means for affixing said personal cooling apparatus to a back rest of a chair.

18. Portable personal cooling apparatus comprising:
    an exterior surface of fibrous material having a fluid holding capacity sufficient to allow continuous evaporation of a fluid;
    an interior surface of waterproof material adapted to avoid wetting of the object to be cooled from fluid on the exterior surface;
    a fluid container means on one of said surfaces for distributing the fluid to the fibrous material;
    a fluid collector means on one of said surfaces for collecting accumulated unevaporated fluid;
    at least one fluid return line means for moving fluid in the fluid collector to the fluid container, at least one of said fluid return lines further including means for preventing fluid from flowing back from the fluid containers to the fluid collectors.

19. The apparatus of claim 18, wherein the means for moving fluid includes use of gravity.

* * * * *